United States Patent
Kauppinen et al.

(10) Patent No.: US 10,420,958 B2
(45) Date of Patent: Sep. 24, 2019

(54) APPARATUS AND METHOD FOR EMPLOYING A MULTI-LEAF COLLIMATOR WHILE ADMINISTERING A RADIATION DOSE

(71) Applicant: Varian Medical Systems International AG, Cham (CH)

(72) Inventors: Juha Kauppinen, Espoo (FI); Esa Kuusela, Espoo (FI)

(73) Assignee: Varian Medical Systems International AG, Steinhausen (CH)

( * ) Notice: Subject to any disclaimer, the term of this patent is extended or adjusted under 35 U.S.C. 154(b) by 548 days.

(21) Appl. No.: 14/865,930

(22) Filed: Sep. 25, 2015

(65) Prior Publication Data

US 2017/0087388 A1    Mar. 30, 2017

(51) Int. Cl.
*A61N 5/10* (2006.01)
*G21K 1/04* (2006.01)

(52) U.S. Cl.
CPC ......... *A61N 5/1077* (2013.01); *A61N 5/1036* (2013.01); *G21K 1/046* (2013.01)

(58) Field of Classification Search
CPC .... G21K 1/046; A61N 5/1036; A61N 5/1045; A61N 5/1047; A61N 5/1077
See application file for complete search history.

(56) References Cited

U.S. PATENT DOCUMENTS

| | | | | |
|---|---|---|---|---|
| 6,052,430 A | * | 4/2000 | Siochi | A61N 5/1042 378/152 |
| 2003/0026384 A1 | * | 2/2003 | Hernandez-Guerra | A61N 5/1042 378/65 |
| 2004/0184578 A1 | * | 9/2004 | Nakano | A61N 5/103 378/65 |
| 2008/0144772 A1 | * | 6/2008 | Yi | A61N 5/1049 378/65 |

FOREIGN PATENT DOCUMENTS

JP    09271520 A    * 10/1997 ............. G21K 1/046

OTHER PUBLICATIONS

JP09271520A Abstract Translation.*

* cited by examiner

*Primary Examiner* — Carrie R Dorna
(74) *Attorney, Agent, or Firm* — Fitch, Even Tabin & Flannery LLP

(57) ABSTRACT

These teachings provide for administering a radiation treatment plan to a patient in a single radiation treatment session using a multi-leaf collimator that is comprised of pairs of selectively movable collimating leaves. By one approach this comprises administering a sequential plurality of modulated radiation doses to the patient, where the sequential plurality of modulated radiation doses comprises at least a substantial majority of a planned total radiation dose for the radiation treatment session and where each modulated radiation dose is administered while modulating a radiation beam (Continued)

with the multi-leaf collimator using a curtain pattern (or, perhaps more typically, a plurality of curtain patterns).

16 Claims, 4 Drawing Sheets

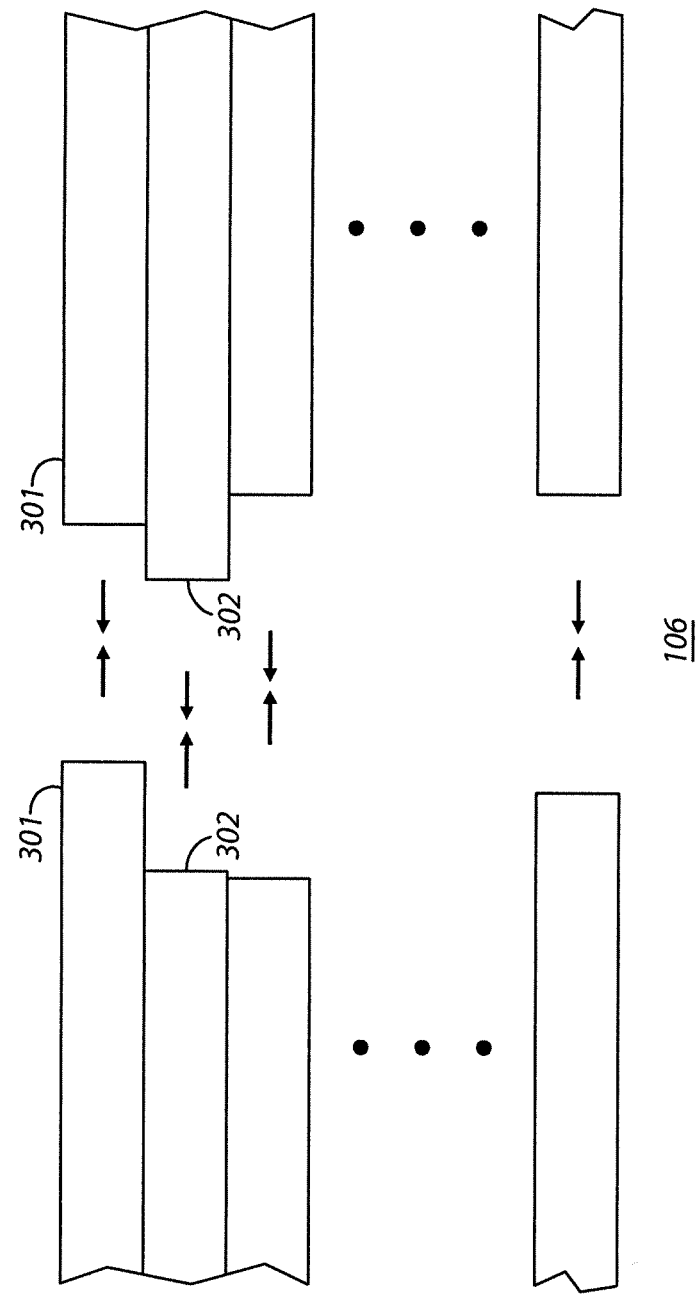

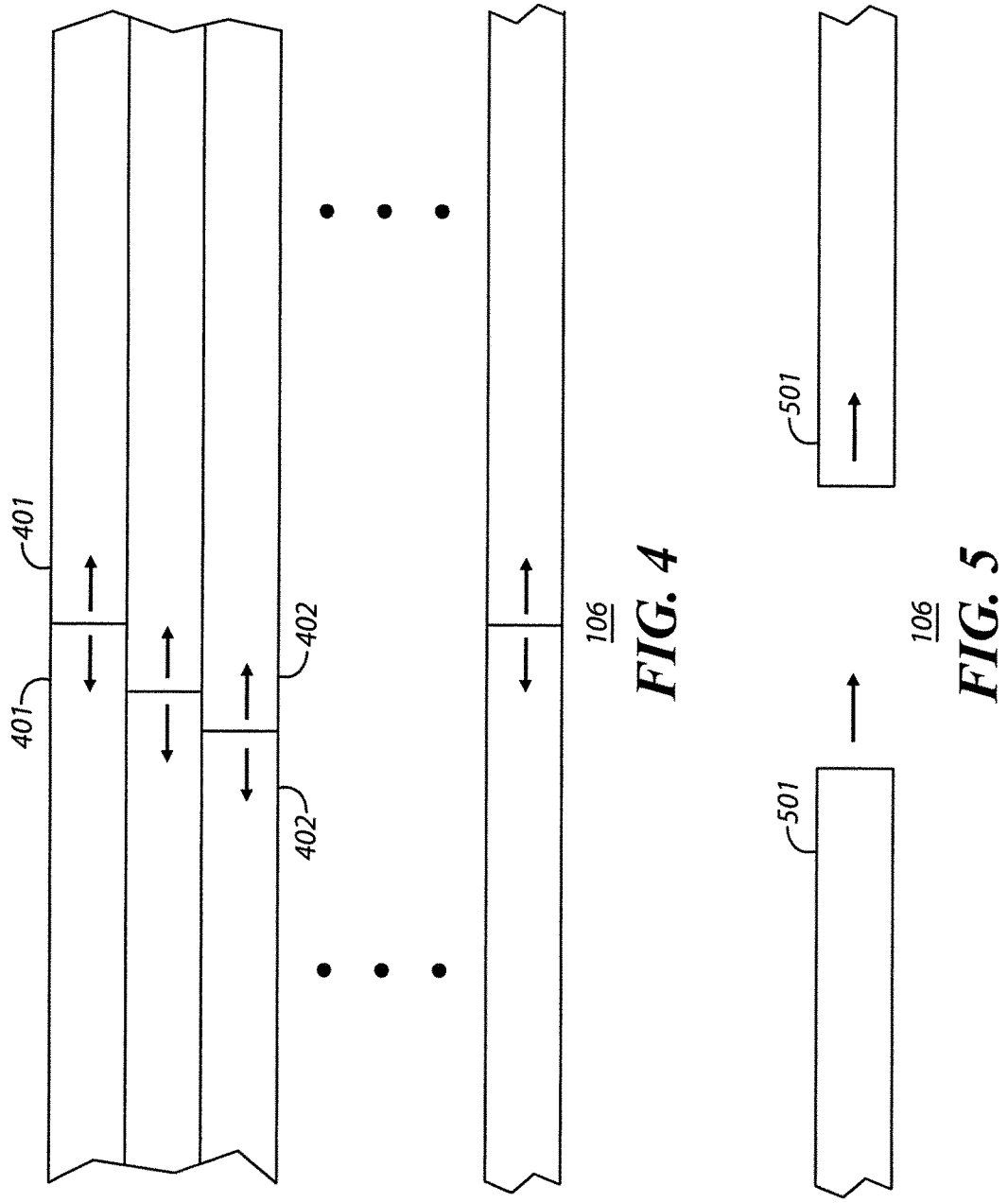

APPARATUS AND METHOD FOR EMPLOYING A MULTI-LEAF COLLIMATOR WHILE ADMINISTERING A RADIATION DOSE

TECHNICAL FIELD

These teachings relate generally to administering therapeutic doses of radiation and more particularly to the use of multi-leaf collimators.

BACKGROUND

Multi-leaf collimators are comprised of a plurality of individual parts (known as "leaves") that are formed of a high atomic numbered material (such as tungsten) that can move independently in and out of the path of the radiation-therapy beam in order to selectively block (and hence shape) the beam. Typically the leaves of a multi-leaf collimator are organized in pairs that are aligned collinearly with respect to one another and that can selectively move towards and away from one another via controlled motors. A typical multi-leaf collimator has many such pairs of leaves, often upwards of twenty, fifty, or even one hundred such pairs.

In many application settings the aperture(s) formed by such a multi-leaf collimator selectively changes during the course of a single radiation treatment session for a given patient (to accommodate, for example, exposing the treatment target to radiation from a variety of different angles (or fields) as occurs during so-called arc therapy).

The sliding window sequencing method is a typical prior art approach to using a multi-leaf collimator that entails creating a leaf-motion pattern where leaf pairs start from a closed or open position on one side of the fluence map and then travel across the fluence. The gap between the leaf tips in a single leaf-pair is modulated during the motion so that every location along the leaf trajectories is exposed to radiation for a length of time that corresponds to the optimal fluence map pixel value at the same location. The sliding window sequencing method is beneficial in that an arbitrary optimal fluence map can often be transformed into leaf sequences with high fidelity and the sequence can be created without imposing any beam holds.

The sliding window technique also has limitations and shortcomings, however. For example, the produced leaf motion patterns are often not very robust for intra-fraction motion during the treatment session. This shortcoming is usually monitored by checking the average leaf-pair opening of the leaf sequence and if necessary the optimal fluence can be re-optimized with criteria that produce smoother fluences. As another example, the sliding window method works best when any leaf can create modulation without restrictions from neighboring leaves. Limiting constraints may occur, however, if the multi-leaf collimator design has leaves in two layers or if neighboring leaves cannot inter-digitate. Such restrictions can usually be solved by further modifying the sliding window pattern, but this solution often increases the necessary monitor units and further reduces the average leaf-pair opening.

Another leaf sequencing method, sometimes referred to as the multiple static segments process, addresses at least some of the foregoing concerns but unfortunately this approach cannot reliably reproduce the optimal fluence with the same fidelity as the sliding window approach and the multiple static segments process also typically requires multiple beam holds that can, in turn, require an unacceptable amount of time for the treatment machine and/or the session parameters of the treatment session.

BRIEF DESCRIPTION OF THE DRAWINGS

The above needs are at least partially met through provision of the apparatus and method for employing a multi-leaf collimator while administering a radiation dose described in the following detailed description, particularly when studied in conjunction with the drawings, wherein:

FIG. 3 comprises a front-elevational detail view as configured in accordance with various embodiments of these teachings;

FIG. 4 comprises a front-elevational view as configured in accordance with various embodiments of these teachings; and FIG. 5 comprises a front-elevational view as configured in accordance with various embodiments of these teachings.

Figure 1:
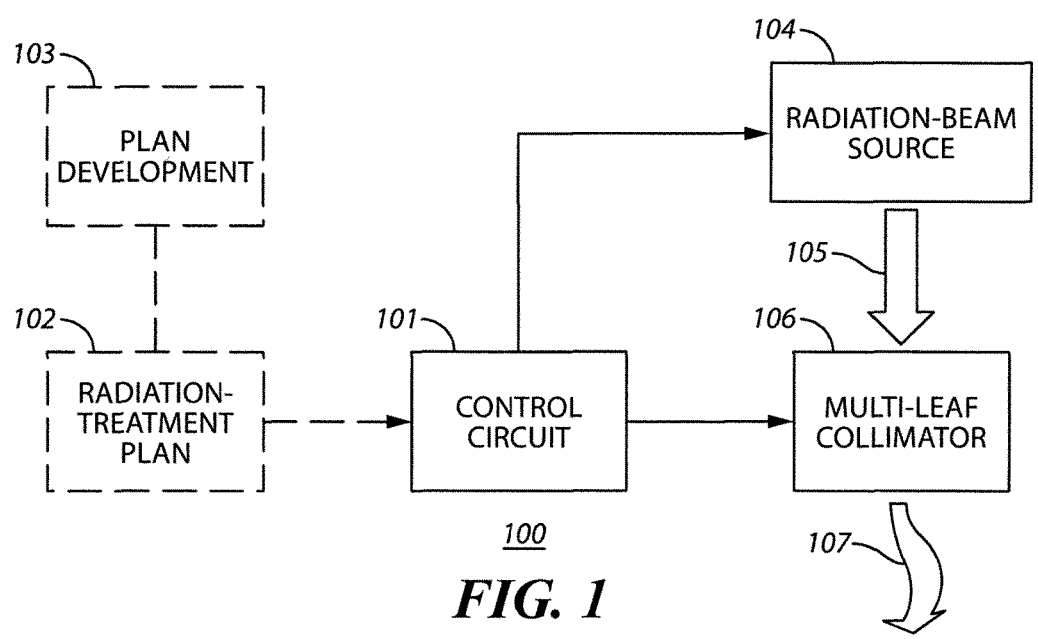
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, these teachings provide for administering a radiation treatment plan to a patient in a single radiation treatment session using a multi-leaf collimator that is comprised of pairs of selectively movable collimating leaves. By one approach this comprises administering a sequential plurality of modulated radiation doses to the patient, where the sequential plurality of modulated radiation doses comprises at least a substantial majority of a planned total radiation dose for the radiation treatment session and where each modulated radiation dose is administered while modulating a radiation beam with the multi-leaf collimator using a curtain pattern (or, perhaps more typically, a plurality of curtain patterns).

By one approach the aforementioned curtain pattern comprises moving collimating leaves of the pairs of collimating leaves towards one another from an opened position. By another approach the curtain pattern comprises moving collimating leaves of the pairs of collimating leaves away from one another from a closed position.

By one approach the radiation treatment plan uses leaf transition sub-sequences between curtain-pattern leaf trajectories. The radiation treatment plan may call for reducing the dose rate during such sub-sequences while avoiding shutting off the radiation beam. Generally speaking these teachings will accommodate administering the sequential plurality of modulation doses in a particular order of treatment that minimizes a total time required for all sub-sequences to move collimating leaves following a completed curtain pattern to prepare to execute a follow-on curtain pattern.

As noted above, the modulated radiation doses that employ a curtain pattern comprise at least a substantial majority of the sequential plurality of modulated radiation doses. These teachings will accommodate using other approaches for a minority of the sequential plurality of modulated radiation doses. For example, these teachings will accommodate including no more than a small portion of the modulated radiation doses that are administered while modulating the radiation beam with the multi-leave collimator using a sliding-window pattern.

So configured, an arbitrary optimal fluence map can be converted into leaf sequences that utilize multiple curtain pattern-based leaf trajectories. These curtain-pattern sequences are typically robust to intra-fraction motion and they are typically not affected as much by the mechanical constraints of the multi-leaf collimator apparatus itself. The radiation beam can be off during the leaf transition sub-sequences but it can be beneficial to avoid beam-holds. Accordingly, by one approach the dose delivered during any given leaf transition sub-sequence can be taken account as part of the overall dose. If desired, this dose can be reduced by reducing the dose rate during the leaf transition sub-sequences without actually shutting the radiation beam off.

These and other benefits may become clearer upon making a thorough review and study of the following detailed description. Referring now to the drawings, and in particular to FIG. 1, an illustrative apparatus 100 that is compatible with many of these teachings will now be presented.

In this example the apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

By one optional approach the control circuit 101 operably couples to a memory. This memory may be integral to the control circuit 101 or can be physically discrete (in whole or in part) from the control circuit 101 as desired. This memory can also be local with respect to the control circuit 101 (where, for example, both share a common circuit board, chassis, power supply, and/or housing) or can be partially or wholly remote with respect to the control circuit 101 (where, for example, the memory is physically located in another facility, metropolitan area, or even country as compared to the control circuit).

By one approach this memory stores a radiation-treatment plan 102 (as developed, for example, by a plan development platform 103 which may be the same as the control circuit 101 or different as desired). In addition to a radiation-treatment plan 102, this memory can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

The control circuit 101 also operably couples to a radiation-beam source 104 that sources (i.e., emits) a corresponding radiation beam 105. This radiation beam 105 is modulated by a multi-leaf collimator 106 to become a modulated radiation beam 107. The multi-leaf collimator 106 operably couples to the control circuit 101 such that its selectively-movable leaves are controllable by the control circuit 101.

Figure 2:
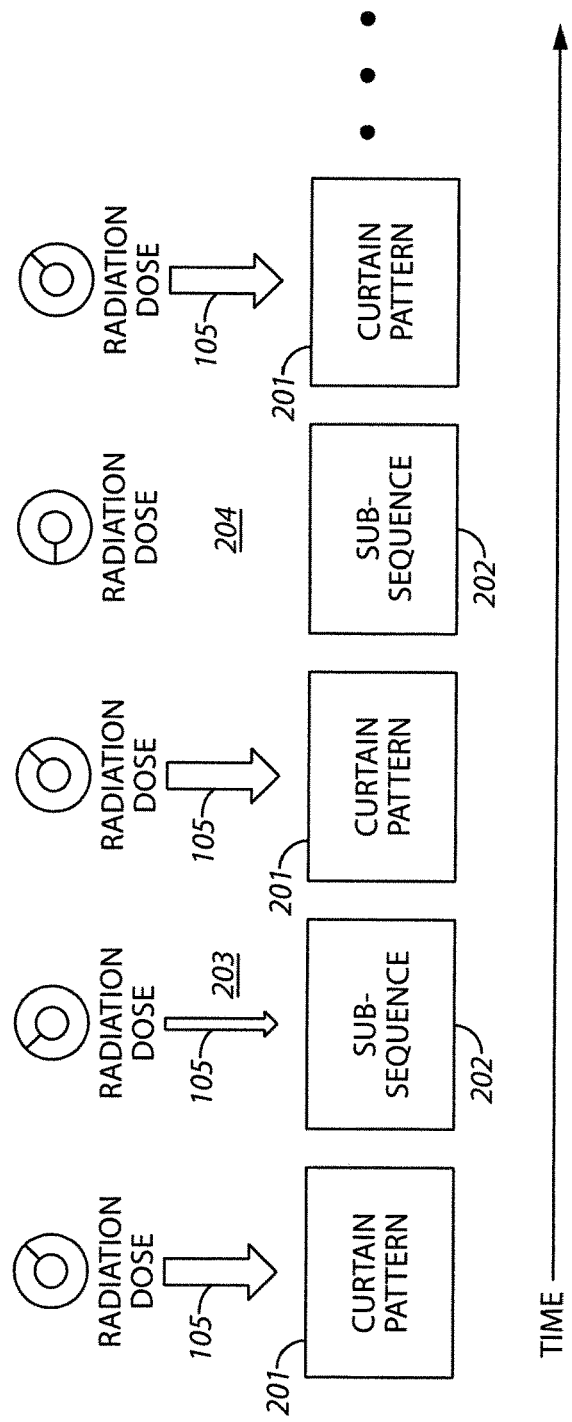
FIG. 2 comprises a time-based schematic representation as configured in accordance with various embodiments of these teachings.

So configured, the control circuit 101 can employ the radiation-beam source 104 and the multi-leaf collimator 106 to administer a radiation treatment plan 102 to a patient in a single radiation treatment session by administering, as illustrated in FIG. 2, a sequential plurality of modulated radiation doses that comprises, at least as a substantial majority of a planned total radiation dose for the radiation treatment session, administering a radiation dose while modulating the radiation beam 105 with the multi-leaf collimator 106 using a corresponding curtain pattern 201. (As used herein, this reference to a "substantial majority" shall be understood to refer to at least seventy-five percent, though there may be application settings where the substantial majority may instead be eighty-five percent, ninety percent, ninety-five percent, or even ninety-eight percent.)

These teachings will accommodate both closing and opening curtain patterns. FIG. 3 presents a simplified illustrative example of a closing curtain pattern. In this example leaves of the pairs of collimating leaves move towards one another from an initial opened position. As illustrated, this approach does not require that all of the leaf pairs begin at the same initial opened position. For example, a first pair of leaves 301 are shown as beginning at one initial opened position while a second pair of leaves 302 are shown as beginning at a second, different initial opened position.

It will also be understood that these teachings do not require that each and every pair of leaves of the multi-leaf collimator must all move during a particular dosing. Instead, these teachings will accommodate having one or more leaf pairs remain stationary (in, for example, a closed orientation). These teachings will also accommodate moving different pairs of leaves at different speeds, such that one pair of leaves might close more quickly or slowly than another pair of leaves.

FIG. 4 presents a simplified illustrative example of an opening curtain pattern. In this example leaves of the pairs of collimating leaves move away one another from an initial closed position. As illustrated, this approach does not require that all of the leaf pairs begin at the same initial closed position. For example, a first pair of leaves 401 are shown as beginning at one initial closed position while a second pair of leaves 402 are shown as beginning at a second, different initial closed position. (As used herein this reference to "closed" shall be understood to refer to being fully closed.)

It will also again be understood that these teachings do not require that each and every pair of leaves of the multi-leaf collimator must all move during a particular dosing. Instead, and again, these teachings will accommodate having one or more leaf pairs remain stationary (in, for example, a closed or opened orientation). These teachings will also again accommodate moving different pairs of leaves at different speeds, such that one pair of leaves might open more quickly or slowly than another pair of leaves.

Referring again to FIGS. 1 and 2, by one approach the aforementioned plan development platform 103 forms the aforementioned radiation-treatment plan 102 by converting an arbitrary optimal fluence map (the formation of which comprises a well-understood area of prior art endeavor) into a plurality of curtain-pattern leaf trajectories for the multi-leaf collimator 106. As already noted above, each of these curtain-pattern leaf trajectories can, and likely will, employ a different curtain pattern 201 as compared to one another.

By one approach all of the curtain patterns 201 may comprise opening curtain patterns. By another approach all of the curtain patterns 201 may comprise closing curtain patterns. By yet another approach the plurality of curtain patterns 201 may comprise a mixture of closing and opening curtain patterns.

If desired, these teachings will accommodate also including no more than a small portion (for example, no more than about twenty-five percent, or fifteen percent, or even five percent or one percent) of the modulated radiation doses that are administered while modulating the radiation beam 105 with the multi-leaf collimator 106 using a sliding-window pattern. (FIG. 5 presents a pair of leaves 501 that are both moving in the same direction and hence illustrates a sliding-window pattern. Those skilled in the art will understand that a sliding-window pattern does not require that both leaves be continuously moving simultaneously with one another nor that both leaves move at the same speed.)

With continued reference to FIG. 2, in some cases the radiation treatment plan is further formed using leaf transition sub-sequences 202 between at least some of the curtain-pattern leaf trajectories 201. These sub-sequences 202 provide an interval during which the collimating leaves can be moved following a completed curtain pattern 201 to prepare to execute a follow-on curtain pattern 201. If desired, a part of the planning process can be determining the specifics of the curtain patterns 201 and/or the particular order in which those curtain patterns 201 are sequentially employed to administer modulated radiation doses in order to minimize a total time required for all sub-sequences 202 to move the collimating leaves following a completed curtain pattern 201 to prepare to execute a subsequent curtain pattern 201.

In at least some cases the duration of the sub-sequences 202 can be shorter, and sometimes considerably shorter, than the respective curtain patterns 201 that sequentially abut the sub-sequence 202.

By one approach the radiation-beam source 104 can remain on during part or all of a given sub-sequence 202 using a same dose rate as is applied when using the curtain patterns 201. By another approach, and as illustrated generally at reference numeral 203, the dose rate of the radiation beam 105 can be reduced but not shut off during a sub-sequence 202. And by yet another approach, and as illustrated generally at reference numeral 204, the radiation beam 105 can be switched off during part or all of a given sub-sequence 202. These teachings will accommodate employing the same dose-rate approach for all of the sub-sequences 202 or using different dose-rate approaches for various ones of the sub-sequences 202.

When forming the radiation-treatment plan 102, by one approach an optimal fluence is divided in order to segregate various portions of the optimal fluence amongst the above-mentioned modulated radiation doses. By one approach, these teachings will additionally accommodate ensuring that the determined apertures are in fact administrable with the specific multi-leave collimator to be used during the treatment session. In some cases this can comprise considering one or more additional dimensions (such as additional leaf layers) by which the multi-leaf collimator 106 can form a given aperture.

So configured the formulation and/or execution of a given radiation-treatment plan 102 can make advantageous use of curtain-pattern approaches that can avoid, at least under some circumstances, some of the limitations and/or frailties of other patterns and or patternless methodologies.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A method to administer a planned total radiation dose according to a radiation treatment plan to a patient in a single radiation treatment session using a multi-leaf collimator comprised of a plurality of pairs of selectively movable collimating leaves, the method comprising:
administering a sequential plurality of modulated radiation doses to the patient, where the sequential plurality of modulated radiation doses includes:
at least one modulated radiation dose administered by modulating the radiation beam with the multi-leaf collimator using a sliding-window pattern to provide some of, but not more than twenty-five percent of, the planned total radiation dose; and
a plurality of modulated radiation doses that are each administered while modulating a radiation beam with the multi-leaf collimator using a curtain pattern and wherein at least one of the plurality of pairs of selectively movable collimating leaves moves at a different speed than another of the pairs of selectively movable collimating leaves to provide a substantial majority of, but not all of, the planned total radiation dose.

2. The method of claim 1 wherein the curtain pattern comprises moving collimating leaves of the pairs of collimating leaves towards one another from an opened position.

3. The method of claim 1 wherein the curtain pattern comprises moving collimating leaves of the pairs of collimating leaves away from one another from a closed position.

4. The method of claim 1 further comprising:
reducing a dose rate during a sub-sequence when moving collimating leaves following a completed curtain pattern to prepare to execute a follow-on curtain pattern.

5. The method of claim 4 wherein reducing the dose rate does not include shutting off the radiation beam.

6. The method of claim 4 wherein administering the sequential plurality of modulated radiation doses comprises administering the sequential plurality of modulation doses in a particular order of treatment that minimizes a total time required for all sub-sequences to move collimating leaves following a completed curtain pattern to prepare to execute a follow-on curtain pattern.

7. The method of claim 1 wherein the radiation treatment plan is formed by converting an arbitrary optimal fluence map into a plurality of curtain-pattern leaf trajectories for the multi-leaf collimator.

8. The method of claim 7 wherein the radiation treatment plan is further formed by using leaf transition sub-sequences between curtain-pattern leaf trajectories.

9. An apparatus to administer a planned total radiation dose according to a radiation treatment plan to a patient in a single radiation treatment session, the apparatus comprising:
- a multi-leaf collimator comprised of a plurality of pairs of selectively movable collimating leaves;
- a radiation-beam source; and
- a control circuit operably coupled to the multi-leaf collimator and the radiation-beam source and configured to administer a sequential plurality of modulated radiation doses to the patient, where the sequential plurality of modulated radiation doses includes:
  - at least one modulated radiation dose administered by modulating the radiation beam with the multi-leaf collimator using a sliding-window pattern to provide some of, but not more than twenty-five percent of, the planned total radiation dose; and
  - a plurality of modulated radiation doses that are each administered while modulating a radiation beam with the multi-leaf collimator using a curtain pattern wherein opposing leaves of at least some of the plurality of pairs are both moving with respect to one another and wherein at least one of the plurality of pairs of selectively movable collimating leaves moves at a different speed than another of the pairs of selectively movable collimating leaves to provide a substantial majority of, but not all of, the planned total radiation dose.

10. The apparatus of claim 9 wherein the curtain pattern comprises moving collimating leaves of the pairs of collimating leaves towards one another from an opened position.

11. The apparatus of claim 9 wherein the curtain pattern comprises moving collimating leaves of the pairs of collimating leaves away from one another from a closed position.

12. The apparatus of claim 9 wherein the control circuit is further configured to reduce a dose rate during a sub-sequence when moving collimating leaves following a completed curtain pattern to prepare to execute a follow-on curtain pattern.

13. The apparatus of claim 12 wherein reducing the dose rate does not include shutting off the radiation beam.

14. The apparatus of claim 12 wherein the control circuit is configured to administer the sequential plurality of modulated radiation doses by administering the sequential plurality of modulation doses in a particular order of treatment that minimizes a total time required for all sub-sequences to move collimating leaves following a completed curtain pattern to prepare to execute a follow-on curtain pattern.

15. The apparatus of claim 9 wherein the radiation treatment plan is formed by converting an arbitrary optimal fluence map into a plurality of curtain-pattern leaf trajectories for the multi-leaf collimator.

16. The apparatus of claim 15 wherein the radiation treatment plan is further formed by using leaf transition sub-sequences between curtain-pattern leaf trajectories.

* * * * *